(12) United States Patent
Kirkpatrick et al.

(10) Patent No.: US 7,442,172 B2
(45) Date of Patent: Oct. 28, 2008

(54) LIGAMENT TENSION GAUGE

(75) Inventors: Lynn A. Kirkpatrick, Columbia City, IN (US); Jacque R. Wilson, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 538 days.

(21) Appl. No.: 10/231,437

(22) Filed: Aug. 29, 2002

(65) Prior Publication Data

US 2004/0044297 A1  Mar. 4, 2004

(51) Int. Cl.
*A61B 5/00* (2006.01)
(52) U.S. Cl. ..................................... 600/595
(58) Field of Classification Search ............... 600/587, 600/595; 606/72, 73, 87–88, 90, 96–98, 606/32, 41; 607/99, 105, 113
See application file for complete search history.

(56) References Cited

U.S. PATENT DOCUMENTS

| | | | | |
|---|---|---|---|---|
| 4,583,554 A | * | 4/1986 | Mittelman et al. | 600/587 |
| 5,213,112 A | * | 5/1993 | Niwa et al. | 600/587 |
| 5,540,696 A | * | 7/1996 | Booth et al. | 606/88 |
| 5,911,695 A | * | 6/1999 | Watkins et al. | 600/587 |
| 5,980,473 A | * | 11/1999 | Korakianitis et al. | 600/587 |
| 6,428,472 B1 | * | 8/2002 | Haas | 600/206 |
| 6,478,799 B1 | * | 11/2002 | Williamson | 606/90 |
| 6,719,709 B2 | * | 4/2004 | Whalen et al. | 600/587 |
| 6,772,012 B2 | * | 8/2004 | Ricart et al. | 607/99 |
| 2001/0049483 A1 | * | 12/2001 | Reay-Young | 600/587 |

* cited by examiner

*Primary Examiner*—Max Hindenburg
*Assistant Examiner*—Fangemonique Smith
(74) *Attorney, Agent, or Firm*—Baker & Daniels LLP

(57) ABSTRACT

An apparatus and method for assessing tension of a ligament in a patient's body with less reliance on a subjective feel of a human examiner.

22 Claims, 4 Drawing Sheets

LIGAMENT TENSION GAUGE

FIELD OF THE INVENTION

The present invention relates generally to the field of orthopaedics, and, more particularly, to an apparatus and method for assessing tension of a ligament in a patient's body with less reliance on a subjective feel of a human examiner.

BACKGROUND

In general, a ligament is a sheet or band of tough, fibrous tissue that helps hold together bones or cartilages at a joint or that helps support an organ. Ligaments can be weakened by injury, disease, genetics, or a combination of such factors. A weakened ligament can lead to pain and deterioration of the associated joint or organ.

Weakened ligaments can sometimes be repaired or replaced by surgery. However, some assessments of ligament tensions, and thus, some determinations of when corrective surgeries have been required, have been undesirably invasive and inaccurate. For example, the posterior cruciate ligament ("PCL") of the human knee joint has been assessed by a procedure in which a surgeon palpates the ligament (touches it by hand). Such an approach not only requires an incision and pathway large enough to allow manipulation of the surgeon's finger, but also relies on a subjective feel of the surgeon to "guestimate" the tension of the ligament.

SUMMARY OF THE INVENTION

The present invention provides an apparatus and method for assessing tension of a ligament in a patient's body with less reliance on a subjective feel of a human examiner. In one embodiment, the apparatus includes a frame separate from the human examiner and a force applicator coupled to the frame. The force applicator is configured to apply a force to the ligament relative to the frame.

In an alternative embodiment, the apparatus includes a frame separate from the human examiner and a means, coupled to the frame, for applying a force to the ligament relative to the frame.

In another alternative embodiment, the apparatus includes a base member configured to be positioned outside the patient's body, a longitudinal sleeve slidably coupled to the base member, and a set screw coupled to the base member. The set screw is extendable to fix a position of the sleeve relative to the base member. The apparatus further includes a longitudinal probe. The longitudinal probe includes a head having a transverse dimension, a cylindrical butt having a first diameter, and a shaft having a second diameter extending through the longitudinal sleeve and between the butt and the head. The transverse dimension of the head and the diameter of the butt are each greater than the diameter of the shaft. The apparatus further includes a coiled spring abutting the butt of the probe, and a see-through cap defining a cylindrical space. The cap includes a rim at an open end of the space, and the rim surrounds a circumference of the shaft. The cap further includes an endwall at a closed end of the space and a sidewall extending between the rim and the endwall. The butt of the probe and the spring are housed in the space with the spring interposed between the butt and the endwall.

In yet another alternative embodiment, the method includes positioning a frame separate from the human examiner, applying a force to the ligament relative to the frame, and indicating a movement, relative to the position of the frame, of the ligament in response to the force.

The above-noted features and advantages of the present invention, as well as additional features and advantages, will be readily apparent to those skilled in the art upon reference to the following detailed description and the accompanying drawings.

DETAILED DESCRIPTION OF EXEMPLARY EMBODIMENT

Figure 1:
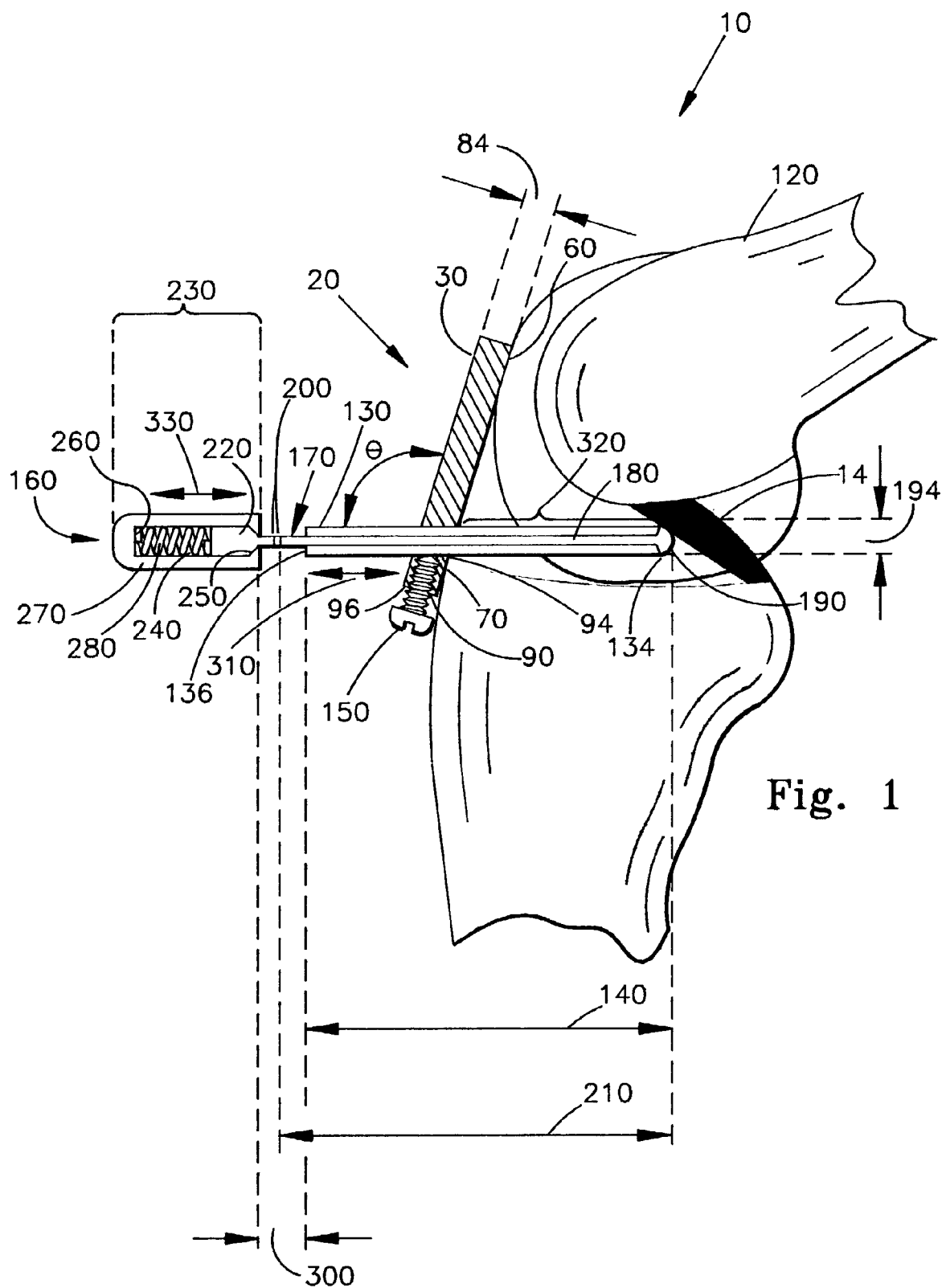
FIG. 1 shows a lateral cross-sectional view of an exemplary embodiment of a ligament tension gauge according to the present invention in a retracted, insertion position (inserted in a human knee joint)

FIG. 1 shows a lateral cross-sectional view of an exemplary embodiment of a ligament tension gauge 10 according to the present invention in a retracted, insertion position (inserted in a human knee joint). Although the exemplary ligament tension gauge 10 is depicted in connection with an assessment of a posterior cruciate ligament ("PCL") 14 of a human knee, it should be appreciated that the exemplary embodiment and/or suitable alternative embodiments may be adapted to provide assessment of an anterior cruciate ligament ("ACL") of a human knee, a ligament of a human elbow, or any other of various ligaments found in humans or other animals.

The exemplary ligament tension gauge 10 includes a frame 20. The frame 20 includes a rigid, longitudinal, plank-shaped base 30 which is made from stainless steel, plastic, or any other material suitable for use in surgical procedures. Also, in the exemplary embodiment the base 30 is reusable and, accordingly, is made suitable for sterilization in an autoclave. However, it should be appreciated that in alternative embodiments the base 30 may be disposable. Further, the base 30 has a longitudinal dimension of about 14.5 cm (5.7 inches) or otherwise sufficient to span between a distal femoral site 60 and a tibial site 70 of a patient's body or between any other suitable reference points. The base 30 has a width 80 (see FIG. 2 and FIG. 3) and a thickness or depth 84 that are large enough to accommodate a suitable threaded longitudinal bore 90 and a suitable smooth transverse bore 94. The bore 94 runs through the depth 84 of the base 30 at an angle $\theta$ relative to the longitude of the base 30. The angle $\theta$ is about 110 degrees or any other value suitable for aligning the ligament tension gauge 10 to project a force onto the ligament (as discussed in further detail below in connection with operations). The bore 90 and the bore 94 intersect within the base 30. The bore 90 begins at end 96 of the base 30 (which is to be positioned proximal to the tibial site 70 and distal from the distal femoral site 60; see operations, discussed below) and ends at its intersection with the bore 94. The width 80 (see FIG. 2) is also small enough to fit within the intercondyloid fossa (i.e., the notch or space) between the lateral condyle 100 (see FIG. 2) and the medial condyle 110 (see FIG. 2) of the distal femur 120.

The frame 20 further includes a rigid, longitudinal sleeve or tube 130 which extends through and slides within the bore 94. The sleeve 130 is made from stainless steel, plastic, or any other material suitable for use in surgical procedures. Also, in the exemplary embodiment the sleeve 130 is reusable and, accordingly, is made suitable for sterilization in an autoclave. It should be appreciated that in alternative embodiments the sleeve 130 may be disposable. Further, the sleeve 130 has a head end 134 and a butt end 136. The sleeve 130 has an outer diameter of about 6.35 mm (0.25 inches) or any other diameter suitable to facilitate insertion into the patient's body. The inner diameter of the sleeve 130 is about half that of its outer diameter. The sleeve 130 has a length 140 of about 20.3 cm (8 inches) or any other length suitable to generally extend through the base 30 and reach the ligament. It is noted that in alternative embodiments, the sleeve 130 may be curved or may be articulated or otherwise bendable to facilitate "snaking" and/or other maneuvering around obstructions and/or to otherwise take a nonlinear path through the patient's body.

The frame 20 further includes a set screw 150 which is screwed into the bore 90. The set screw 150 is made from stainless steel, plastic, or any other material suitable for use in surgical procedures. Also, in the exemplary embodiment the set screw 150 is reusable and, accordingly, is made suitable for sterilization in an autoclave. It should be appreciated that in alternative embodiments the set screw 150 may be disposable. Further, the set screw 150 is long enough to extend into the intersection of the bore 90 and the bore 94.

The exemplary ligament tension gauge 10 further includes a force applicator 160. In general, the force applicator 160 is configured to apply a force to the ligament relative to the frame 20. In the exemplary embodiment the force applicator 160 is configured to apply a thrusting or pushing force to the ligament. It should be appreciated that in alternative embodiments the force applicator 160 may be configured to apply a pulling force or any other suitable force to the ligament. In the exemplary embodiment, the force applicator 160 includes a probe 170. The probe 170 has a longitudinal shaft 180 that extends through and slides within the sleeve 130 of the frame 20. The probe 170 is made from stainless steel, plastic, or any other material suitable for use in surgical procedures. Also, in the exemplary embodiment the probe 170 is reusable and, accordingly, is made suitable for sterilization in an autoclave. It should be appreciated that in alternative embodiments the probe 170 may be disposable. The shaft 180 has rigidity, curvature, and/or bendability compatible with the sleeve 130.

The probe 170 further includes a head 190 connected to the shaft 180 at an end proximal to the head end 134 of the sleeve 130. The head 190 is generally shaped to facilitate insertion into the patient and to maintain centering (i.e., reduce lateral slipping) and avoid injuries while pushing against the ligament. Accordingly, the head 190 is generally convex and has an ovular base portion with a maximum first transverse dimension 194 roughly equal to the outer diameter of the sleeve 130 and with a maximum second transverse dimension 196 (see FIG. 3) roughly equal to the inner diameter of the sleeve 130, or the head 190 has any other shape and dimensions suitable to facilitate centering of the head 190 on the ligament and reduce slipping of the head 190 from engagement with the ligament during operation.

Circumferential marks or bands 200 are painted on or carved into the shaft 180 at a distance 210 from the head 190. The distance 210 is greater than the length 140 of the sleeve 130, such that the marks 200 are not hidden within the sleeve 130 when the head 190 abuts the head end 134. Further, the marks 200 are located within a spacing 300 which is discussed further below.

A cylindrical butt 220 of the probe 170 is spaced apart from the head 190 by the shaft 180. The diameter of the butt 220 is greater than the inner diameter of the sleeve 130.

The force applicator 160 further includes a transparent cylindrical cap 230 which defines a cylindrical space 240. The cap 230 is made from plastic or any other transparent material suitable for use in surgical procedures. Also, in the exemplary embodiment the cap 230 is reusable and, accordingly, is made suitable for sterilization in an autoclave. It should be appreciated that in alternative embodiments the cap 230 may be disposable. Further, the cap 230 has a rim 250 at an open end, an endwall 260 at a closed end, and a sidewall 270 which extends between the rim 250 and at the endwall 260. The transparency of the cap 230 facilitates observation of the position of the marks 200 during operation (discussed in further detail below). It is noted that in alternative embodiments the cap 230 and/or other components of the present invention may have suitable slits, perforations, openings, dimensions, and/or other features which facilitate observation of the marks 200, and thus, it should be appreciated that in some alternative embodiments the cap 230 may be made from stainless steel, opaque plastic, or any other opaque material suitable for use in surgical procedures. Moreover, it should be appreciated that in operation (discussed further below) the position of the marks 200 indicates a position of the head 190 and thus a position or deflection of the ligament in response to the force projected onto the ligament by the head 190. To this end, it is noted that in alternative embodiments the position of the head 190 and/or the deflection of the ligament may be measured and/or indicated by electronic or electromechanical equipment or any other suitable manner in addition to or in lieu of the marks 200.

The force applicator 160 further includes a resilient member 280 which is housed along with the butt 220 in the space 240 such that the resilient member 280 is interposed between the butt 220 and the end wall 260. The resilient member 280 is a coiled stainless steel spring, a comparable rubber cylinder, a comparable compressible gas filled cylinder, or any other resilient material or assembly of any length and/or spring rate suitable for desirable operation of the ligament tension gauge 10. Also, in the exemplary embodiment the resilient member 280 is reusable and, accordingly, is made suitable for sterilization in an autoclave. It should be appreciated that in alternative embodiments the resilient member 280 may be disposable.

The sleeve 130 and the components of the force applicator 160 are also configured such that the spacing 300 between the butt end 136 and the rim 250 (when the head 190 abuts the head end 134 and the rim 250 abuts the butt 220) is equal to or less than a relative travel of the end wall 260 (towards the butt 220) necessary to fully compress the resilient member 280. This configuration protects against over extensions and projections of excessive force by the head 190 (discussed in further detail below).

Figure 2:
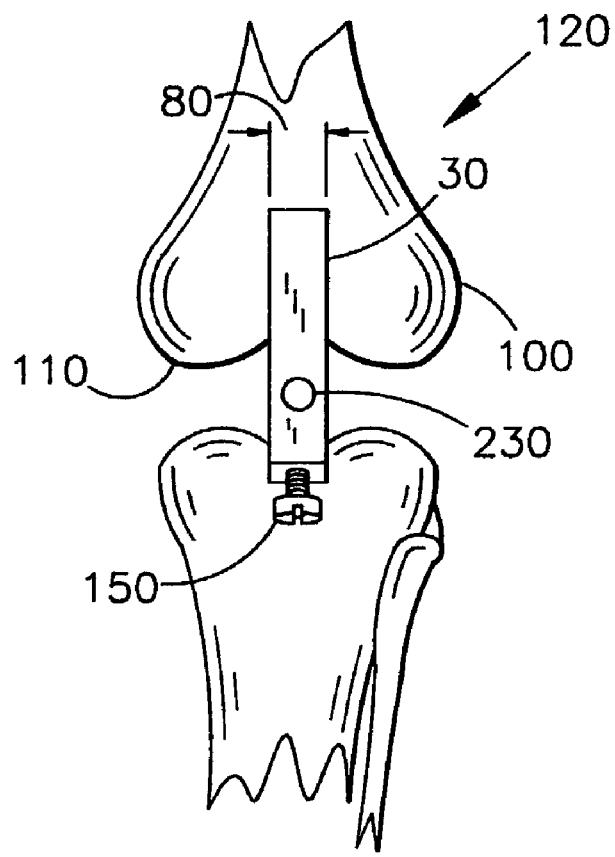
FIG. 2 shows an anterior view of the ligament tension gauge of FIG. 1 (still inserted in the knee)

FIG. 2 shows an anterior view of the ligament tension gauge 10 of FIG. 1 (still inserted in the knee). The width 80 of the base 30 is discernable in FIG. 2. Views of the set screw 150 and the cap 230 are also included in FIG. 2. The distal femur 120 (including the lateral condyle 100 and the medial condyle 110) of the patient are also shown in FIG. 2.

Figure 3:
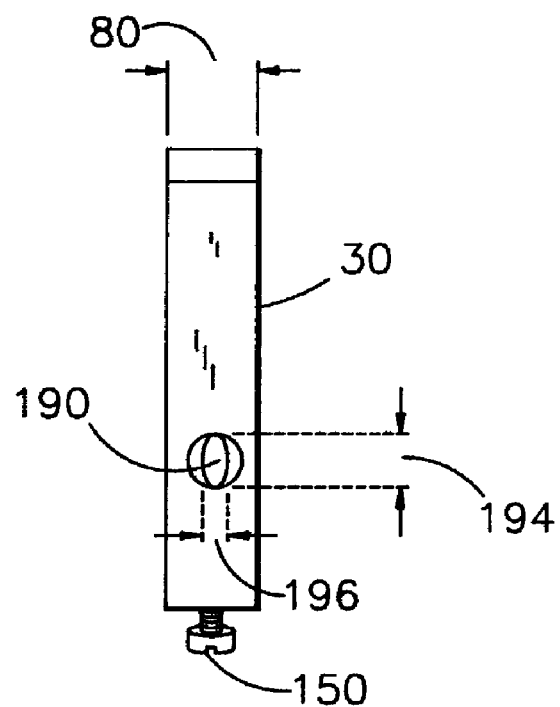
FIG. 3 shows a posterior view of the ligament tension gauge of FIG. 1 (not inserted in the knee)

FIG. 3 shows a posterior view of the ligament tension gauge 10 of FIG. 1 (not inserted in the knee). The width 80 of the base 30, the maximum first transverse dimension 194 of the head 190, and the maximum second transverse dimension 196 of the head 190 are discernable in FIG. 3.

Referring again to FIG. 1, in operation of the exemplary ligament tension gauge 10 a surgeon or other user loosens the set screw 150. The user performs whatever surgical procedures are required to provide a pathway for insertion of the sleeve 130 and the head 190 into the patient's body up to the location of the ligament to be assessed. For assessment of the PCL 14 with the exemplary ligament tension gauge 10, these procedures may include everting (i.e., partially disconnecting and swinging aside) the patient's patella or any other suitable procedures. It should be appreciated that alternative embodiments may lend themselves to different procedures for providing access to the ligament to be assessed.

To continue with assessment of the PCL 14, the user holds the base 30 against the distal femoral site 60 (within the intercondyloid fossa, see FIG. 2) and against the tibial site 70. This alignment of the base 30 in turn aligns the sleeve 130, which in turn aligns the probe 170. Then, the user extends the head end 134 of the sleeve 130 (see the directional lines 310) and the head 190 of the probe 170 a distance 320 from the base 30 into the patient's body to make contact with the ligament without deflecting or projecting a substantial force onto the ligament while the head 190 abuts the head end 134. In addition to or in lieu of the naked eye, it should be appreciated that the user may employ a video camera or any other suitable imaging or proximity detection technology to facilitate the determination of the distance 320.

After the distance 320 is determined, the user tightens the set screw 150 to secure the position of the sleeve 130 (including the head end 134) relative to the base 30. Then the user presses on the cap 230 to actuate the force applicator 160, which moves the shaft 180 (see directional lines 330) and extends the head 190 of the probe 170 away from head end 134 of the sleeve 130.

Figure 4:
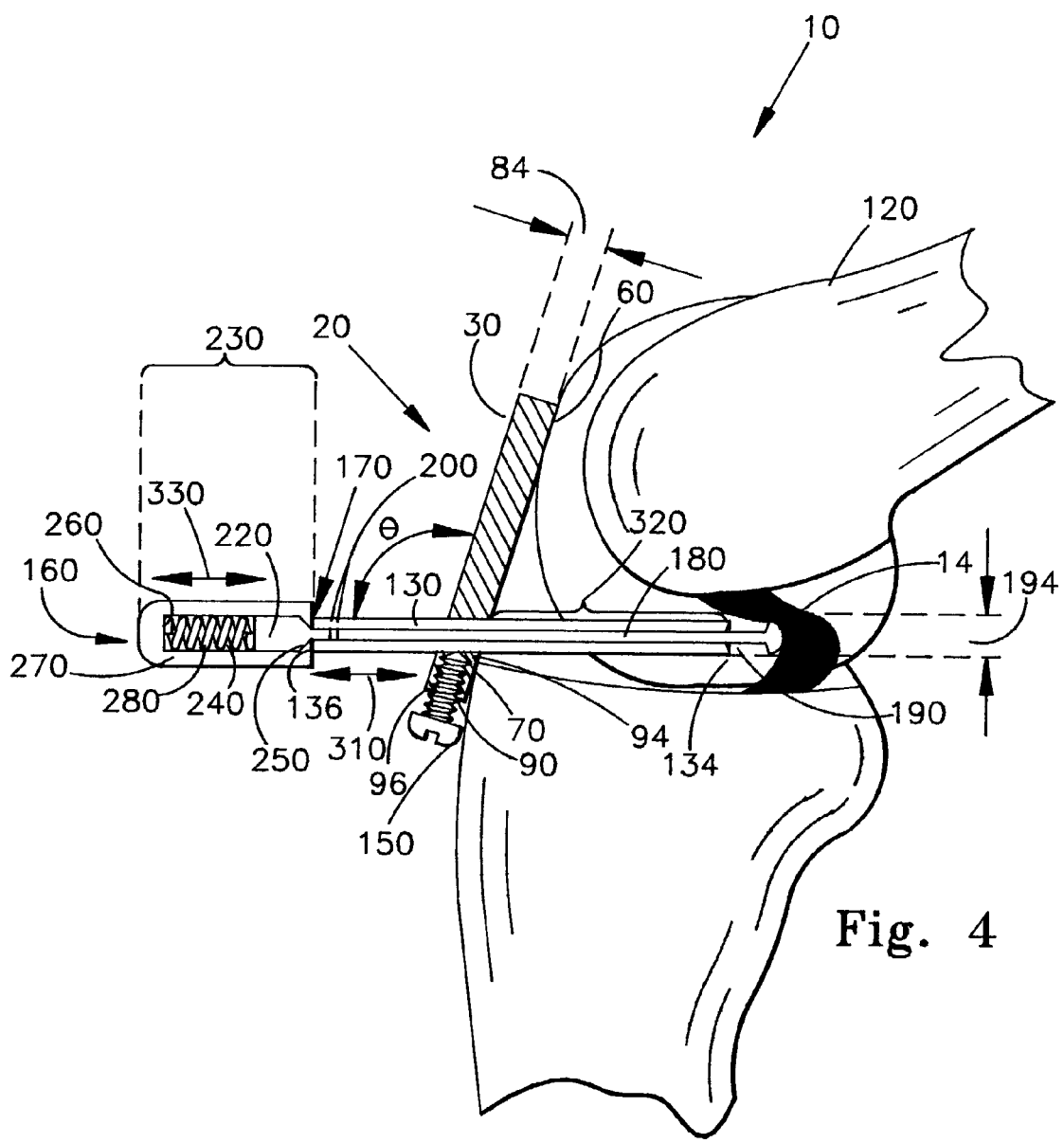
FIG. 4 shows a lateral cross-sectional view of the ligament tension gauge of FIG. 1 in an extended, assessment position (inserted in a knee and with a "loose" PCL)

FIG. 4 shows a lateral cross-sectional view of the ligament tension gauge 10 of FIG. 1 in an extended, assessment position (inserted in a knee and with a "loose" PCL). The ligament tension gauge 10 indicates that the ligament under assessment is "loose" by the marks 200 advancing into the sleeve 130 when the force applicator 160 is actuated. Because the user can see through the cap 230, the user can discern the position of the marks 200 even when the cap 230 abuts the butt end 136 of the sleeve 130. Meanwhile, the limited travel of the cap 230 (by abutment of the cap 230 against the butt end 136 of the sleeve 130) works to limit the extension of the head 190, and thus, somewhat safeguards a loose ligament and/or surrounding tissues from excessive stretching and/or other potential injuries which might result from over deflection.

Figure 5:
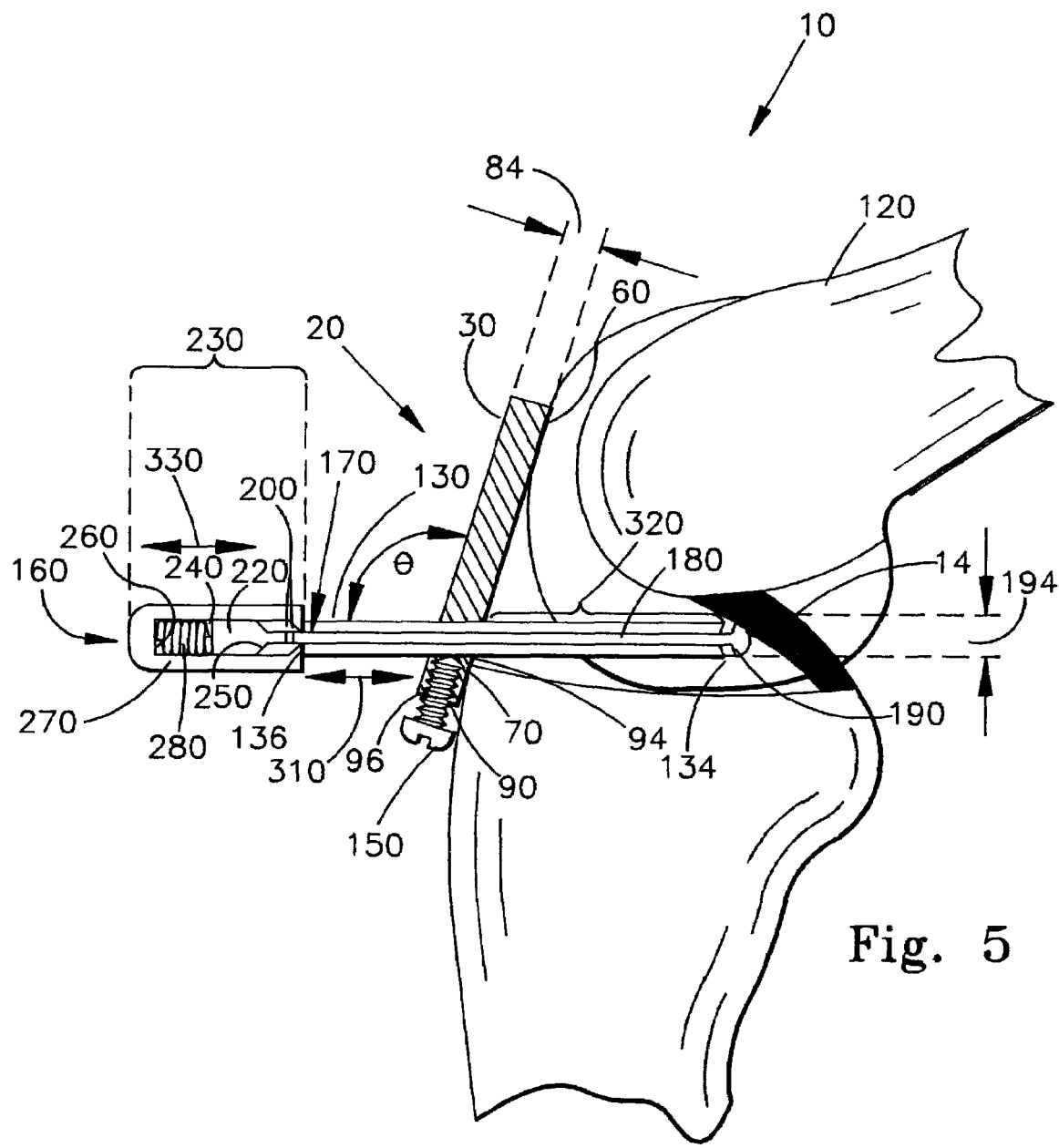
FIG. 5 shows a lateral cross-sectional view of the ligament tension gauge of FIG. 1 in an extended, assessment position (inserted in a knee and with a "tight" PCL).

FIG. 5 shows a lateral cross-sectional view of the ligament tension gauge 10 of FIG. 1 in an extended, assessment position (inserted in a knee and with a "tight" PCL). The ligament tension gauge 10 indicates that the ligament under assessment is "tight" by the marks 200 remaining outside the sleeve 130 when the force applicator 160 is actuated. Because the user can see through the cap 230, the user can discern the position of the marks 200 even when the cap 230 abuts the butt end 136 of the sleeve 130. Meanwhile, the limited compression of the resilient member 280 (by abutment of the cap 230 against the butt end 136 of the sleeve 130) works to limit the force projected onto the ligament by the head 190, and thus, somewhat safeguards a tight ligament and/or surrounding tissues from tearing and/or other potential injuries which might result from an application of excessive force.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. An apparatus of assessing tension of a ligament at a joint in a patient's body, the apparatus comprising:
    a base having a surface abuttable with a portion of the patient's body;
    a tubular housing mounted to the base, the tubular housing defining an opening transverse to the surface;
    a probe having an elongated shaft with a first end, a second end, and a longitudinal axis between the first and second ends, the probe being mounted for translation within the opening of the tubular housing transverse to the surface and along the longitudinal axis of the shaft, the probe extending from the base such that the first end is axially engage able with the ligament; and
    means for translating the probe axially within the opening of the tubular housing toward the ligament to apply a force to the ligament by pressing the first end axially against the ligament.

2. The apparatus of claim 1, wherein the means for translating the probe comprises a force applicator coupled to the probe, the force applicator including a first end extending from the second end of the probe, and a resilient member positioned between the second end of the probe and the first end of the force applicator, the force applicator being operable to compress the resilient member and transmit an axial force to the second end of the probe along the shaft axis.

3. The apparatus of claim 2, wherein the force applicator comprises a hollow cap having a closed end corresponding to the first end of the force applicator and an open end, the open end and engaging the second end of the probe in sliding relationship, the cap containing the resilient member between the closed end and the second end of the probe such that the cap is sidable on the probe from the second end of the probe toward the first end of the probe a predetermined distance until the resilient member is fully compressed.

4. The apparatus of claim 3, wherein the hollow cap includes at least one of a transparent portion and a slotted portion to permit observing the probe shaft.

5. The apparatus of claim 4, wherein the resilient member includes a coiled spring.

6. The apparatus of claim 2, wherein the tubular housing comprises a tubular member mounted for axial translation relative to the base, the tubular member defining an axial bore, the probe shaft being mounted in the axial bore of the tubular member for axial translation relative to the tubular member, the force applicator being operable to cause the probe shaft to translate within the tubular member until the force applicator abuts the tubular member.

7. The apparatus of claim 1, wherein the base is configured to simultaneously abut a distal femoral site and a proximal tibial site.

8. The apparatus of claim 1, wherein the probe includes a bendable portion.

9. The apparatus of claim 6, further comprising a locking mechanism engageable with the tubular member to lock the tubular member's position relative to the base.

10. The apparatus of claim 9, wherein the locking mechanism comprises a screw threadably mounted to the base and rotatably advanceable to engage the tubular member.

11. The apparatus of claim 6, wherein the force applicator and the tubular member cooperate to limit at least one of a magnitude of the force and a deflection imparted on the ligament by the probe.

12. An apparatus for assessing tension of a ligament in a patient's body, the apparatus comprising:
    a base member configured to be positioned outside the patient's body;

a longitudinal sleeve slidably coupled to the base member;

a locking mechanism mounted to the base member, the locking mechanism being operable to fix a position of the sleeve relative to the base member;

a longitudinal probe having a first end and a second end, the first end being engageable with the ligament, the probe extending through the longitudinal sleeve;

a spring member abutting the second end of the probe; and a cap defining a cylindrical space, tbe cap including an open end, the cap further including an endwall at a closed end of the cylindrical space and a sidewall extending between the open end and the endwall, the second end of the probe and the spring being housed in the cylindrical space with the spring interposed between the second end of the probe and the endwall.

13. The apparatus of claim 12, wherein the sleeve has a length, and the probe includes a mark at a distance from the first end, the distance being greater than the length of the sleeve.

14. The apparatus of claim 12, wherein the cap includes a transparent portion.

15. The apparatus of claim 12, wherein the cap includes a slotted portion.

16. A method for assessing tension of a ligament in a patient's body, the method comprising the steps of:
   abutting a base against a portion of the patient's body outside of a joint;
   translating a probe transversely relative to the base into the joint to engage the ligament;
   translating the probe further into the joint to further engage the ligament and apply a force to the ligament relative to the base; and
   indicating ligament tension by a movement, relative to the base, of the ligament in response to the force.

17. The method of claim 16 further comprising:
   positioning a tubular member relative to the base to extend the tubular member into the joint to a position adjacent to the ligament; and
   locking the position of the tubular member relative to the base, wherein translating a probe comprises translating the probe within the tubular member.

18. The method of claim 17 wherein translating the probe comprises depressing a resilient force applicator to transmit a translational force to the probe, the resilient force applicator acting to limit the force applied to the ligament.

19. The method of claim 18 wherein the tubular member has a length, and the probe includes a shaft having a first end engageable with the ligament and a second end opposite the first end, the shaft including a mark at a distance from the first end, the distance being greater than the length of the tubular member such that ligament tension is indicated upon depressing the force applicator, the apparatus indicating a loose ligament by the mark translating into the tubular method and the apparatus indicating a tight ligament by the mark remaining outside of the tubular member while the resilient member compresses.

20. The method of claim 18 wherein the force applicator abuts the tubular member to limit the deflection imparted to the ligament.

21. The apparatus of claim 6, wherein the tubular member has a length and the shaft includes a mark at a distance from the first end of the shaft, the distance being greater than the length of the tubular member such that, upon depressing the force applicator, the apparatus indicates a loose ligament by the mark translating into the tubular member and the apparatus indicates a tight ligament by the mark remaining outside of the tubular member while the resilient member compresses.

22. The apparatus of claim 7, wherein the probe extends through the base at an angle that permits the base to abut the distal femoral site and the proximal tibial site while the probe extends into engagement with the ligament.

\* \* \* \* \*